United States Patent [19]
Chern et al.

[11] Patent Number: 5,193,395
[45] Date of Patent: Mar. 16, 1993

[54] METHOD AND APPARATUS FOR DETERMINATION OF MATERIAL RESIDUAL STRESS

[75] Inventors: Engmin J. Chern, Columbia; Yury Flom, Silver Spring, both of Md.

[73] Assignee: The United States of America as represented by the Administrator of the National Aeronautics and Space Administration, Washington, D.C.

[21] Appl. No.: 801,141

[22] Filed: Dec. 2, 1991

[51] Int. Cl.$^5$ .............................................. G01N 3/32
[52] U.S. Cl. ........................................ 73/779; 73/797; 324/222
[58] Field of Search ............... 324/222, 209, 207.15, 324/654, 656; 73/787, 779, 797

[56] References Cited

U.S. PATENT DOCUMENTS

| | | | |
|---|---|---|---|
| 3,969,928 | 7/1976 | Zarka | 73/88 R |
| 4,249,423 | 2/1981 | Viertl et al. | 73/783 |
| 4,528,856 | 7/1985 | Junker et al. | 73/779 |
| 4,852,397 | 8/1989 | Haggag | 73/82 |
| 5,055,784 | 10/1991 | Jaeger et al. | 324/654 X |

FOREIGN PATENT DOCUMENTS 2194336  3/1988  United Kingdom .

OTHER PUBLICATIONS

Determination of Residual Stresses in Sheet Metal Mar. 1981.
A Technique for Measuring Residual Stresses Jul. 1981.

Primary Examiner—Jerry W. Myracle
Attorney, Agent, or Firm—R. Dennis Marchant; Guy M. Miller; Paul S. Clohan, Jr.

[57] ABSTRACT

A device for the determination of residual stress in a material sample consisting of a sensor coil, adjacent the material sample, whose resistance varies according to the amount of stress within the material sample, a mechanical push-pull machine for imparting a gradually increasing compressional and tensional force on the material sample, and an impedance gain/phase analyzer and PC for sending an input signal to and receiving an input signal from the sensor coil. The PC will measure and record the change in resistance of the sensor coil and the corresponding amount of strain of the sample. The PC will then determine from the measurements of change of resistance and corresponding strain of the sample the point at which the resistance of the sensor coil is at a minimum and the corresponding value and type of strain of the sample at that minimum resistance point thereby enabling a calculation of the residual stress in the sample.

6 Claims, 3 Drawing Sheets

METHOD AND APPARATUS FOR DETERMINATION OF MATERIAL RESIDUAL STRESS

ORIGIN OF THE INVENTION

The invention described herein was made by employees of the U.S. Government, and may be manufactured and used by or for the Government for governmental purposes without the payment of any royalties thereon or therefor.

TECHNICAL FIELD

This invention relates to Non Destructive Inspection techniques and more particularly to a method and device for the determination of the initial stress state of a material specimen.

BACKGROUND ART

Methods of measuring residual stresses have been in use for some time, and fall generally into two categories: destructive and non-destructive. Destructive methods required that the specimen was cut-up by hole drilling, electrical discharge machining (EDM), sand blasting, or trepanning. Hole drilling was a common method but had the undesirable feature that the drill worked the surface locally and built-in its own stresses. The EDM method while good was awkward to implement. Non-destructive methods have relied on some change in physical property when the material is stressed, e.g., the velocity of ultrasonic waves is affected. Unfortunately the velocity is affected far more by small variations in materials properties which makes the system useless for stress measurement on anything but pure metals. X-rays have also been used but can only measure crystals near the surface and this is a complex method which can be handled well only in the laboratory while the real requirement is to know the stresses over a greater depth, namely those which would influence the initiation and propagation of cracks.

STATEMENT OF THE INVENTION

It is therefore an object of the present invention to provide a method and an apparatus for the determination of the residual stress in materials that overcomes the limitations found in prior art methods and devices.

The foregoing objects and others are achieved by providing a method and apparatus for the determination of material residual stress utilizing three major hardware components; a mechanical compression/tension tester, a data acquisition/control device, and an impedance gain/phase analyzer. Other sub-components are a sensor coil mounted on the surface of the material specimen, and cabling to interconnect the components.

The novelty of the present invention lies in the discovery that the sensor coil resistance and reactance monotonically increases and decreases with respect to externally applied stresses regardless of direction, i.e., tension or compression. If plotted on a graph of resistance vs. strain, the point at which the resistance of the sensor coil is at a minimum indicates the zero stress state of the specimen. The residual stress is then the strain (compression or tension) indicated on the graph at this minimum resistance point.

In the present invention, the impedance gain/phase analyzer, well known in the art, is connected to the sensor coil via a cable and to the data acquisition/control device via another cable. The impedance gain/phase analyzer is also connected to the mechanical test machine through the data acquisition/control device. The data acquisition/control device acts as the system controller and is used to control the mechanical stress/strain machine and to process data from the impedance gain/phase analyzer. The data acquisition device/system controller can be an IBM PC or the equivalent.

DETAILED DESCRIPTION OF THE INVENTION

Figure 2:
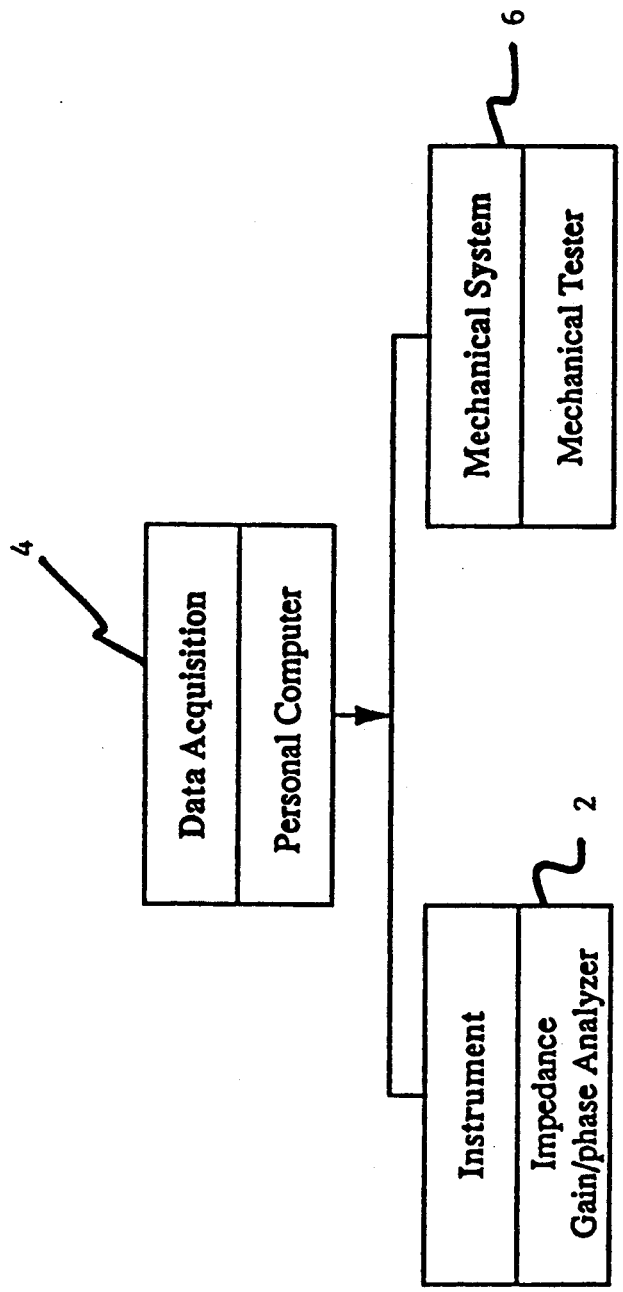
FIG. 2 is a block diagram of a device according to the present invention.
Figure 3:
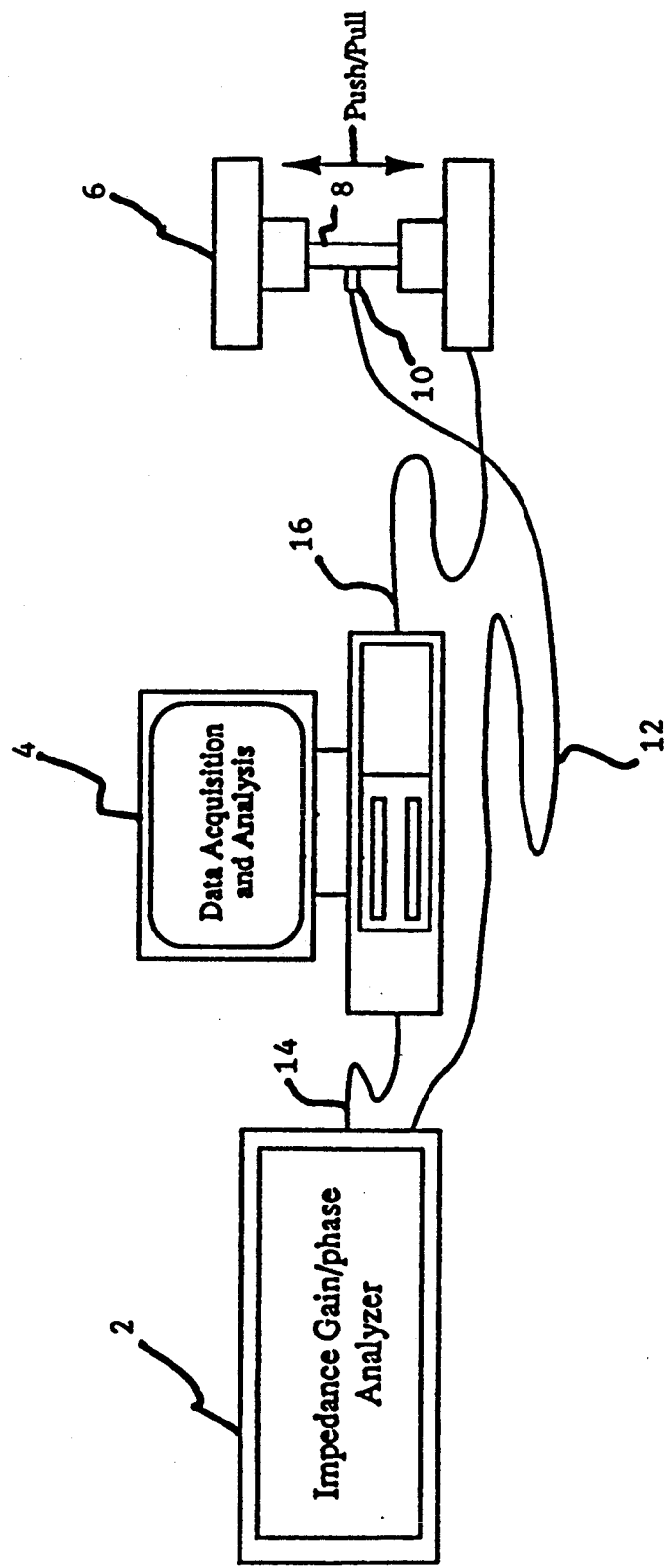
FIG. 3 is a schematic diagram of a device according to the present invention.

The invention consists of a method and apparatus for determination of material residual stress utilizing three major hardware components as shown in FIG. 2, which is a block diagram of the present inventive system for material residual stress determination. The three major components are: a mechanical tester 6, a data acquisition device 4, and an impedance gain/phase analyzer 2. Other sub-components, shown schematically in FIG. 3 are sensor coil 10, mounted on the surface of material specimen 8, and cabling 12, 14, 16.

Figure 1:
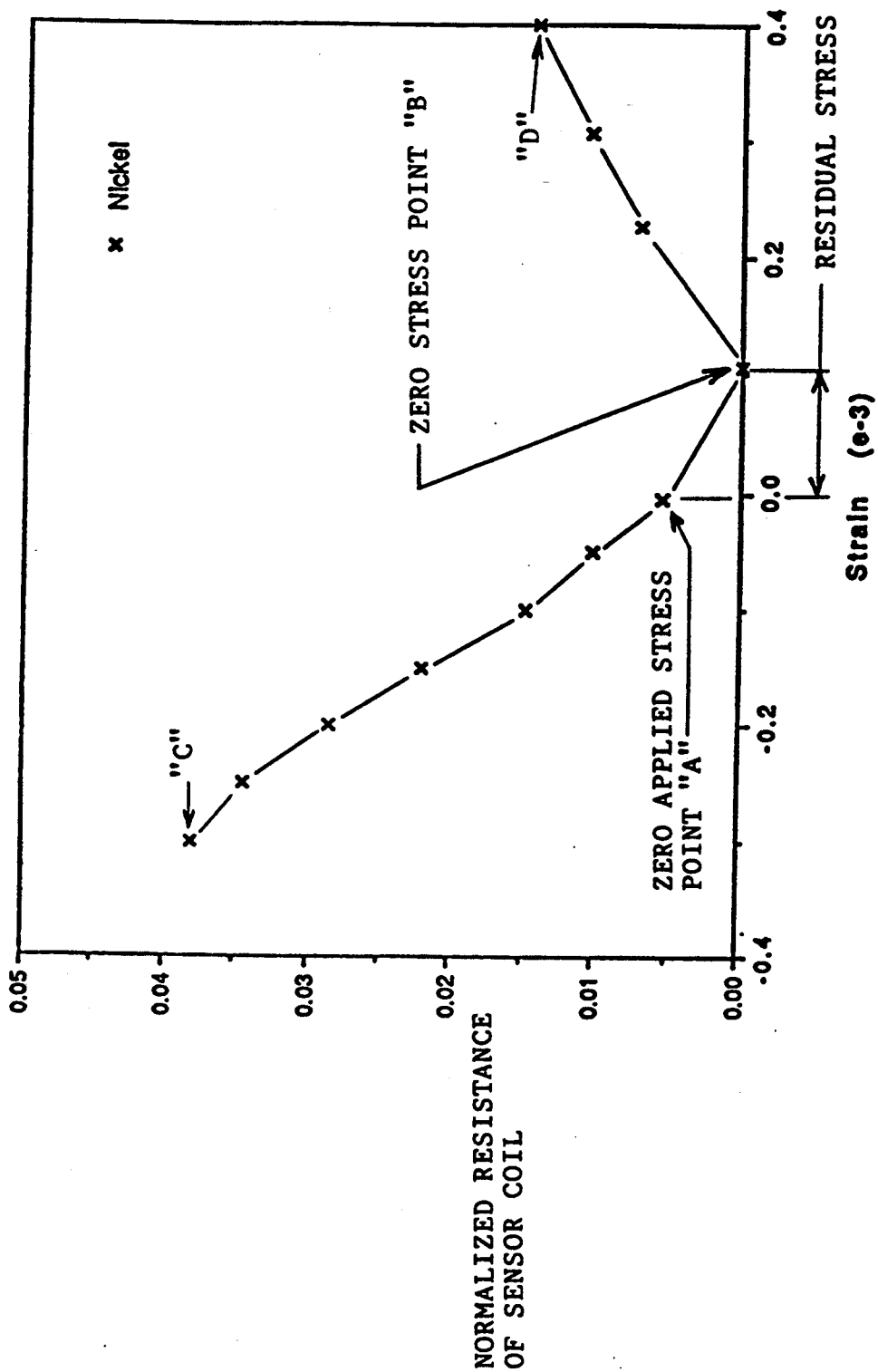
FIG. 1 is a graph of the sensor coil normalized resistance vs. strain when compression and tension is applied to a material sample made from nickel.

The novelty of the present invention lies in the discovery that sensor coil 10 resistance and reactance monotonically increases/decreases with respect to externally applied stresses regardless of the direction, i.e., tension or compression. This relationship is shown in FIG. 1 for a material sample 8 made from nickel where the sensor coil 10 normalized resistance measurements, obtained from the data acquisition device 4, are plotted against the applied compressional and tensional forces exerted on specimen 8 by the mechanical tester 6. Starting from point "A", the point at which tester 6 is applying no stress to sample 8 (zero applied stress point), it can be seen that the normalized resistance of sensor coil 10 has some positive value. As tension is applied to sample 8, the resistance of coil 10 increases to a maximum value at point "C". As the tension is released, the resistance of coil 10 returns to its former value at zero applied stress point "A". As compression is applied to sample 8, the resistance of coil 10 decreases from its value at point "A" until reaching some minimum value at the zero stress point "B". As compression continues to be applied to sample 8, the resistance of coil 10 will then start to increase again from point "B" until it reaches some maximum value at point "D". The residual stress in sample 8 is thus equal to the compressional strain imparted by tester 6 on sample 8 at point "B", the point at which the resistance of coil 10 is at a minimum. This point could just as easily occur at a tensional value in other samples.

In the present invention, an impedance gain/phase analyzer 2, such as is well known in the art, is connected to sensor coil 10, via cable 12, to excite sensor coil 10 and to monitor its resistance, and to data acquisition device 4 via cable 14. Impedance gain/phase analyzer 2 is also connected indirectly to mechanical tester 6 through data acquisition device 4. Data acquisition device 4 not only excites coil 10 but also acts as the system controller and is used to control mechanical tester 6 and to process data from impedance gain/phase analyzer 2. Data acquisition device/system controller 4 can be an IBM series 386 PC or the equivalent. An example of a suitable impedance gain/phase analyzer 2 is an HP 4194A analyzer connected by an IEEE488 bus to data acquisition device/system controller 4. A typical sensor coil 10 is a Staveley Instruments, Inc. NORTEC-3551 100 kHz pencil probe. Mechanical tester 6 can be an Instron, an MTS, or equivalent universal tester. Cables 12, 14, 16 are well known in this art.

To those skilled in the art, many modifications and variations of the present invention are possible in light of the above teachings. It is therefore to be understood that the present invention can be practiced otherwise than as specifically described herein and still will be within the spirit and scope of the appended claims.

I claim:

1. A method for the determination of residual stress in a material sample comprising the steps of:

placing a sensing means whose resistance varies according to the amount of stress within said material sample adjacent said material sample;

imparting a gradually increasing compressional force on said material sample;

sending an input signal to and receiving an input signal from said sensing means;

measuring and recording the change in resistance of said sensing means and the corresponding amount of compressional strain of said sample;

imparting a gradually increasing tensional force on said material sample;

measuring and recording the change in resistance of said sensing means and the corresponding amount of tensional strain of said sample;

determining from said measurements of change of resistance and corresponding strain of said sample the point at which the resistance of said sensing means is at a minimum and the corresponding value and type of strain of said sample at that minimum resistance point thereby enabling a calculation of the residual stress in said sample.

2. The method of claim 1 wherein said steps of sending an input signal to and receiving an input signal from said sensing means and measuring and recording the change in resistance of said sensing means and the corresponding amount of compressional and tensional strain of said sample is implemented by an impedance gain/phase analyzer in conjunction with a data acquisition and analysis computer.

3. The method of claim 2 wherein said steps of imparting a gradually increasing compressional force and a gradually increasing tensional force on said material sample is implemented by a mechanical push-pull machine.

4. A device for the determination of residual stress in a material sample comprising:

sensing means adjacent said material sample whose resistance varies according to the amount of stress within said material sample;

means for imparting a gradually increasing compressional force on said material sample;

means for sending an input signal to and receiving an input signal from said sensing means;

means for measuring and recording the change in resistance of said sensing means and the corresponding amount of compressional strain of said sample;

means for imparting a gradually increasing tensional force on said material sample;

means for measuring and recording the change in resistance of said sensing means and the corresponding amount of tensional strain of said sample;

means for determining from said measurements of change of resistance and corresponding strain of said sample the point at which the resistance of said sensing means is at a minimum and the corresponding value and type of strain of said sample at that minimum resistance point thereby enabling a calculation of the residual stress in said sample.

5. The device of claim 4 wherein said means for sending an input signal to and receiving an input signal from said sensing means and measuring and recording the change in resistance of said sensing means and the corresponding amount of compressional and tensional strain of said sample comprises an impedance gain/phase analyzer in conjunction with a data acquisition and analysis computer.

6. The device of claim 5 wherein said means for imparting a gradually increasing compressional force and a gradually increasing tensional force on said material sample comprises a mechanical push-pull machine.

* * * * *